United States Patent [19]

Richter

[11] Patent Number: 4,594,904
[45] Date of Patent: Jun. 17, 1986

[54] SAMPLING VALVE FOR A FIXED BED REACTOR COAL GASIFICATION PLANT

[75] Inventor: Artur Richter, Mülheim, Fed. Rep. of Germany

[73] Assignee: Ruhrkohle Aktiengesellschaft, Essen, Fed. Rep. of Germany

[21] Appl. No.: 624,104

[22] Filed: Jun. 25, 1984

[30] Foreign Application Priority Data

Jun. 24, 1983 [DE] Fed. Rep. of Germany ....... 3322798

[51] Int. Cl.⁴ .............................................. G01N 1/22
[52] U.S. Cl. ................................ 73/863.86; 73/863.11
[58] Field of Search ........... 73/863.86, 863.81, 863.11, 73/863.12; 251/264, 273, 88, 84; 137/240, 341, 340, 246.11, 246, 334, 237, 339

[56] References Cited

U.S. PATENT DOCUMENTS

| | | | |
|---|---|---|---|
| 2,556,557 | 6/1951 | Schweitzer, Jr. | 251/27 |
| 2,682,277 | 6/1954 | Marshall et al. | 137/384 |
| 2,688,423 | 9/1954 | Davis | 137/246 X |
| 3,486,382 | 12/1969 | Vivares et al. | |
| 3,517,557 | 6/1970 | Granger et al. | |
| 3,651,825 | 3/1972 | Sury | 137/240 |
| 3,761,053 | 9/1973 | Bedo et al. | 251/88 |
| 3,913,602 | 10/1975 | Yoon | 137/341 X |
| 3,985,300 | 10/1976 | Pinney | 137/239 X |
| 4,070,161 | 1/1978 | Horter | 137/246 X |
| 4,114,851 | 9/1978 | Shivak et al. | 251/264 X |
| 4,128,008 | 12/1978 | Linenberg | 73/863.12 |
| 4,133,744 | 1/1979 | Mitchell et al. | 208/254 H X |
| 4,365,563 | 12/1982 | Wu | 137/240 X |
| 4,436,106 | 3/1984 | Tuchenhagen et al. | 137/240 |

FOREIGN PATENT DOCUMENTS

| | | | |
|---|---|---|---|
| 1106572 | 5/1961 | Fed. Rep. of Germany. | |
| 2752284 | 6/1978 | Fed. Rep. of Germany | 73/863.86 |
| 56876 | 3/1969 | Poland | 73/863.86 |
| 867823 | 5/1961 | United Kingdom. | |

Primary Examiner—Stewart J. Levy
Assistant Examiner—Tom Noland
Attorney, Agent, or Firm—Nils H. Ljungman

[57] ABSTRACT

With sampling valves for gas streams or liquids, especially in coal gasification plants and with the sampling valve located close to the reactor, the functional reliability of the valve and the identity of the samples with the crude gas stream are ensured by heating and/or flushing the sampling valve. The valve has several embodiments which include features which can be used in various combinations, for example, the valve stem can include a heater, a passage for the introduction of a flushing and/or heating medium into the valve chamber. The valve housing can include a second chamber therein through which a heating medium can be circulated or by which pressure differentials on the valve chamber can be minimized.

7 Claims, 3 Drawing Figures

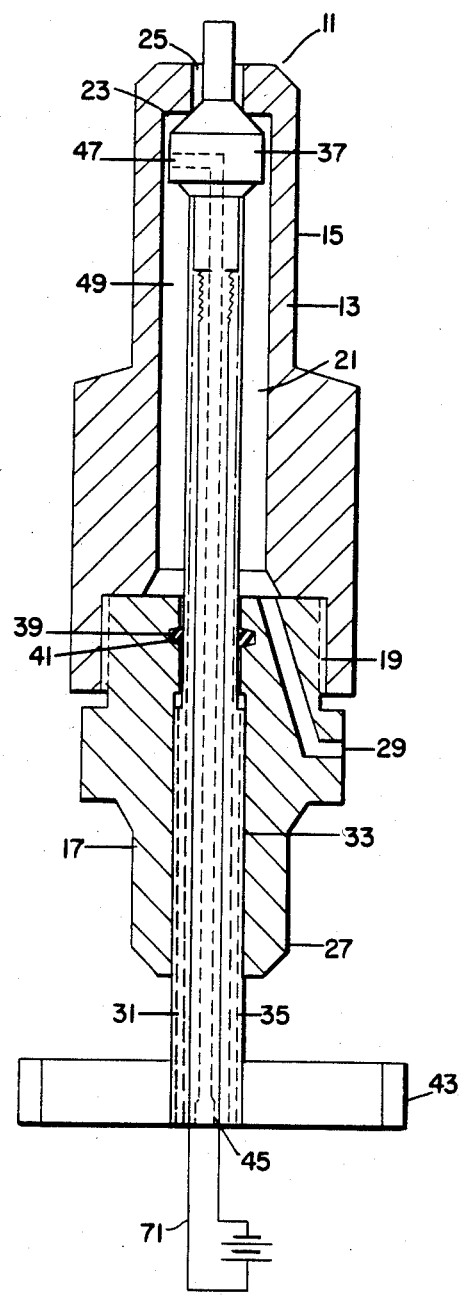
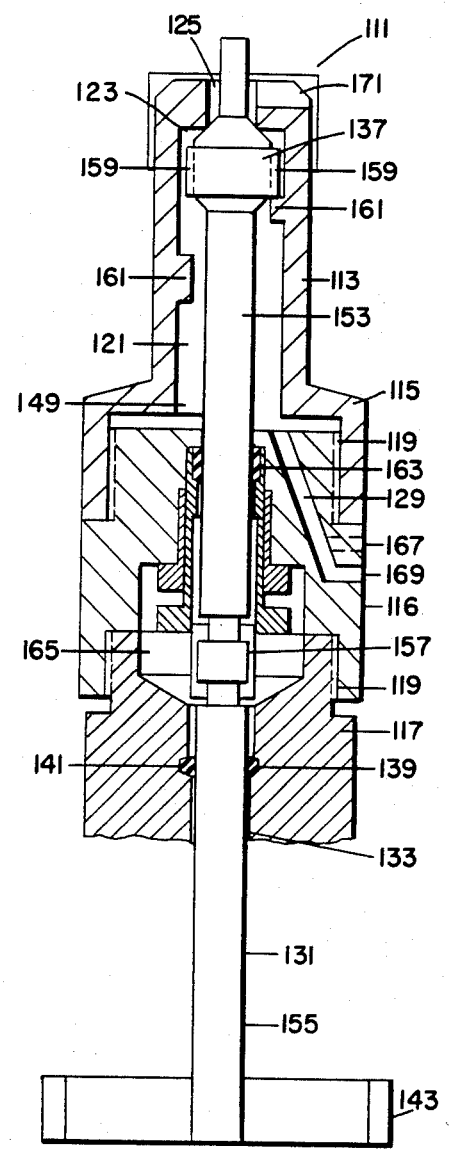

SAMPLING VALVE FOR A FIXED BED REACTOR COAL GASIFICATION PLANT

RELATED APPLICATION

This application is related to the application entitled "Sampling Valve for Fluidized Bed Reactor Coal Gasification Plants" Ser. No. 624,103 filed June 25, 1984 and assigned to the same assignee as the present application and now abandoned.

BACKGROUND OF THE INVENTION

1. Field of the Invention

The invention concerns a sampling valve for liquid and gas streams, especially for coal gasification plants with a fixed bed and with a high solids content in the crude gas, reactors with gas streams having a high temperature level and the danger of condensation.

2. Discussion of the Prior Art

In particular, the Lurgi gasification process belongs to the coal gasification plants in question. In the process developed by Lurgi, the lumpy coal is preferably gasified at a pressure of 30 bars, but it can also be gasified at a pressure of up to 100 bars and above. In the process, the coal is gasified with steam and oxygen in a quaisi static heap (or bed) on a hearth. The coal is introduced into the gas generator via a lock (or charging valve) and a distributor. The gasifying agent flows in under the hearth, as a result of which a good distribution and uniform gasification is obtained. The coal passes through various zones which merge one into the other. The coal is dried, low-temperature carbonized, gasified in turn by the rising gases and finally burned. The resulting ash is removed, almost carbon-free, via a lock. The generators are surrounded by a water jacket. The steam produced therein is fed to the gasifying agent. The gas produced leaves the upper part of the generator. The easily cracked tar products are carried out with the crude gas together with the undecomposed steam and dust.

In the succeeding condensation and condensate-separation installations, a thick dust-containing tar is deposited which, as a rule, is fed back via a circuit into the generator. The dust is gasified and the finally obtained almost dust-free tar can be further processed with the other condensation products.

The optimization of the above-described procedures requires the considerable use of automatic control technology. As a result, the control of gasification reactors involves serious problems. The composition of the crude gas has, in this case, shown itself to be a control quantity which cannot be ignored. Hitherto, in order to obtain a sample, the desired amount of sample was drawn off at the earliest possible time, subsequent to the saturation and purification of the crude gas, from the gas exiting from the coal gasification reactor, using for this purpose a suitable connecting pipe. The connecting pipe discharges via an intermediate sampling valve into the gas pipe connected to the outlet side of the reactor or to the radiation and/or convection cooler connected to the outlet side of the reactor. Due to the pressure reigning in the gasification plant, crude gas flows into the connecting pipe on opening the sampling valve. The amount of sample obtained depends on the amount of time which elapses between opening and closing the sampling valve which closes the connecting pipe at its mouth.

However, the gas drawn-off as the sample is frequently not representative of the crude gas, the sampling being rendered difficult on account of the high temperature of the crude gas, its high pressure and the amount of solids in the gas which tend to precipitate when the temperature is reduced. In particular, the condensing-out of heavy hydrocarbons and chlorides impairs the trouble-proof operation of the sampling valves. This leads to an additional arrangement of sampling valves on the downstream side with their associated connecting pipes. In practice, these connecting places for the taking of samples are associated with the gas purifying stages. Apart from the drawback of having a serious delay in the measurement of the composition of the crude gas, there is associated with these locations the additional danger of condensation and hence concomitant blockages or falsifications of the drawn gas samples.

It is therefore an object of the invention to provide a sampling valve which can function reliably when located as closely as possible to the reactor.

SUMMARY OF THE INVENTION

In accordance with the invention, this task is accomplished by means of a heating arrangement and/or the purification-flushing of the sampling valve. The condensation of constituents of the gas is opposed by heating the sampling valve. In addition, unforeseen condensations, which can result from large time intervals between samplings, are obviated by the purification-flushing in accordance with the invention. The purification-flushing operation is carried out in such a way that, instead of the purifying agent for the crude gas stream, a flushing liquid is, as a rule, forced through the sampling valves and the associated pipe system.

It is especially advantageous to combine the heating, in accordance with the invention, of the sampling valve and the purification-flushing by arranging a heating unit on the flushing pipe used for the purification-flush. With the heating installation so arranged, it is possible to preheat the flushing agent and the sampling valve with through-streaming flushing agent that in a subsequent sampling, the incoming crude gas does not encounter cold condensation-initiating wall surfaces in the valve housing.

In a further embodiment of the invention, the sampling valve is provided with a valve body which is inserted in an axial direction in the valve housing and closes an entrance-opening in the valve housing leading to the sampling pipe. At the same time, the flushing pipe discharges at the location where the valve body makes its connection behind the closure face in the valve housing in the entrance opening. This ensures two effects. One of these effects is the most complete action of the flushing agent on all the surfaces of the sampling valve which come into contact with the crude gas. The other is the use of the crude gas entrance opening in the sampling valve as a duct for the flushing agent. In addition, the valve stem of the sampling valve is made, in the usual way, in the form of a cone and is located in the entrance opening, the arrangement being such that a gap is provided between the surface of the cone and the interior surface of the entrance opening, and the valve stem is movably held at the rear end in the valve housing. With the multi-sectional stem of the invention, a rotatable connection is provided between the parts, and the valve cone is led in the peripheral direction. This ensures that the sealing surfaces on the valve cone and in the sampling valve's housing cannot engage each other in rotation, but only make contact with each other by translation.

The stem is provided with a packing seal and, in the event of extreme pressure and/or temperature conditions, can be connected to the flushing pipe at the recess in the valve housing for the seal. This makes possible a step-by-step reduction in the pressure or a selective use of seals.

BRIEF DESCRIPTIONS OF THE DRAWINGS

The above, as well as other features and advantages of the present invention, will become apparent through consideration of the detailed description of the invention in conjunction with the several drawings in which:

FIG. 1 is a sectional view of a first embodiment of a sampling valve incorporating the teachings of this invention, FIG. 2 is a sectional view of an alternative embodiment of a sampling valve all in accordance with the teachings of this invention, and FIG. 3 is a schematical representation of a sampling valve incorporating the features of this invention shown in combination with a flow diagram for a sampling operation.

DETAILED DESCRIPTION OF THE INVENTION

Figure 3:
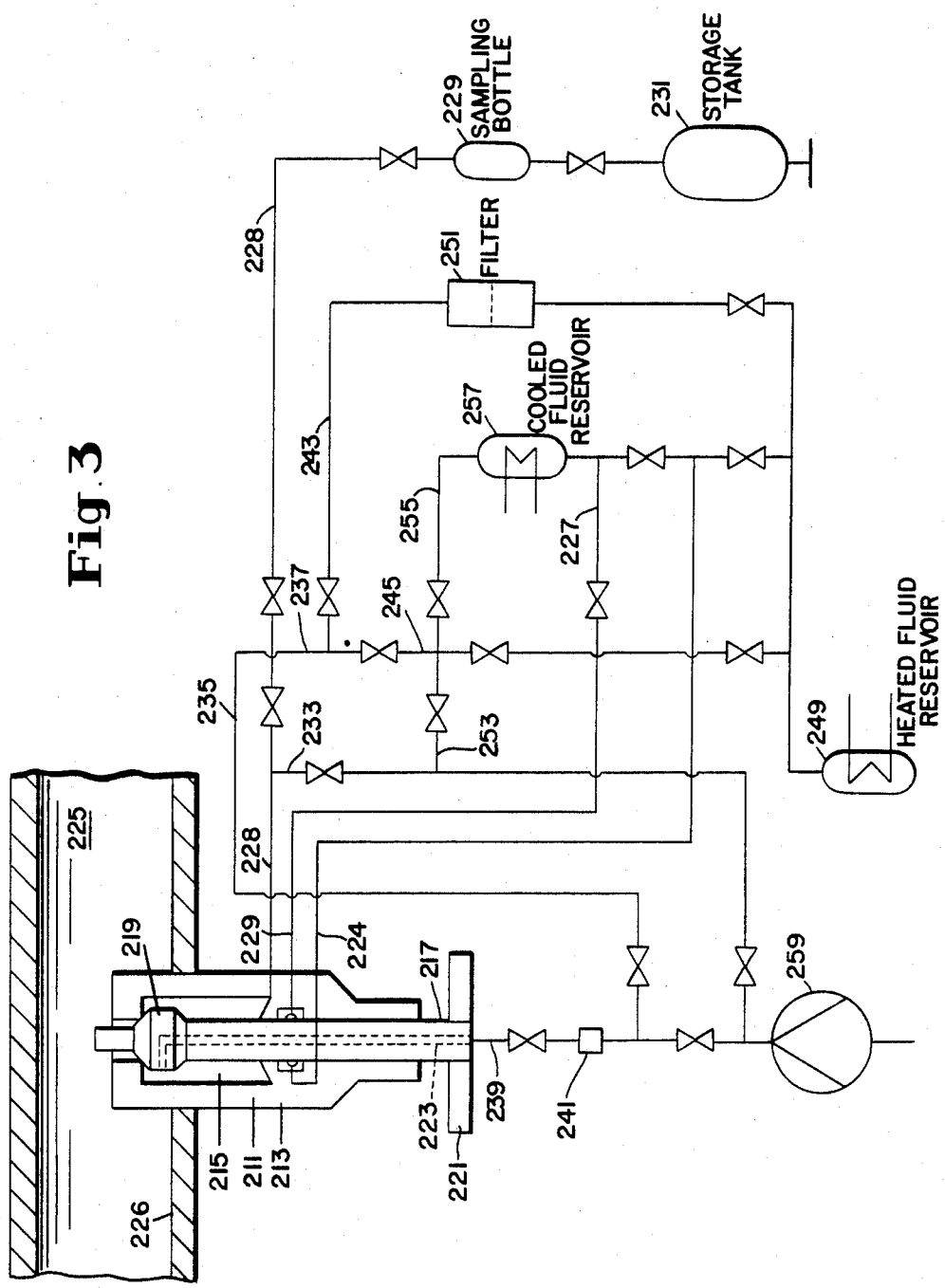

A first embodiment of a sampling valve incorporating the teachings of this invention is shown in sectional view in FIG. 1 and is generally indicated by the reference character 11. The sampling valve 11 has a housing 13 consisting of a first section 15 and a second section 17 which are threadedly interconnected as at 19. The valve housing defines a valve chamber 21 which chamber has a first end 23 with an opening therein at 25 and a second end 27 opposite the first end 23. Also in the valve housing 13 at a location remote from the opening 25 is a second opening 29. A first portion of the housing 15 forms the lodgement or seat of the sampling valve 13 at the desired place in the pipe conveying the crude gas as will be described in detail below. A valve stem means generally indicated at 31 is mounted in the housing 13 so as to extend through the valve chamber 21 and seat in the opening 25 of valve housing portion 15. Valve housing portion 17 includes a bore 33 therein which threadedly receives the portion 35 of the valve stem proximate the hand wheel or spur gear 43 in order to effect the axial displacement of the valve shutter 37 relative to the opening 25 by rotation thereof. The bore 33 also includes a machined groove 39 adapted to receive therein a sealing means 41 such as an O-ring or the like. The valve stem means 31 is actuated by means of a hand wheel or a spur gear 43 which is firmly mounted on the end of the stem which projects out of the valve housing 13.

The valve stem means 31 includes a generally axially disposed bore or passage 45 which extends substantially the length of the stem means and intersects a radially disposed channel 47 in the valve shutter 37. The bore 45 provides communication with the valve chamber 21 for a hot medium or a flushing agent which is forced therethrough and can exit from the valve shutter and be fed eventually to the remote opening 29 in the housing portion 17. The valve chamber 21 is defined by the outer periphery of the stem means 31 and valve shutter 37 and the interior wall 49 of the valve housing 13 which surrounds the stem means.

Thus as can be seen in the first embodiment of the invention as shown in FIG. 1, a heating or flushing agent can enter the valve chamber through the bores 45 and 47 of the stem means, flush the valve chamber and exit from the valve chamber. When a sample is being withdrawn by means of this valve, the valve shutter is axially spaced from the opening in the housing through the rotation of the valve stem and a sample is drawn into the valve chamber and then drawn therefrom through the second opening in the valve housing a valve stem resistive heater means 71 can be operably associated with the appropriate electrical power source to maintain the required sampling valve temperature.

An alternative embodiment of the sampling valve of this invention is generally indicated by the reference character 111. A valve housing 113 comprises three sections: a first or upper section 115, a middle section 116, and a lower section 117, all of which sections are threadedly interconnected as at 119. A valve chamber 121 is defined by the upper valve section 113 and the middle valve section 116. At the upper reaches 123 of the first valve section 113 is disposed an opening 125 through which the sampled constituents enter the valve chamber. A second opening 129 is provided in the middle valve housing portion 116 at a location remote from the first opening to provide a means for the withdrawal of at least the sample constituent. A valve stem means 131 is disposed in the valve housing 113 and is threadedly interconnected with the third portion 117 of the valve housing for axially displaced movement therein. A groove or channel 139 is circumferentially disposed within the bore 133 of housing portion 117 and provides a seat for a seal means 141 for the like therein. The stem means 131 is actuated by means of a hand wheel or a spur gear 143 which is firmly mounted on the end of the stem which projects out of the valve housing 113. The valve stem means 131 includes a valve shutter 137.

Contrary to the embodiment shown in FIG. 1, sampling valve 111 has a valve stem means 131 consisting of two basic sections 153 and 155 which are interconnected by a coupling means 157 which allows independent rotational movement of section 155 with respect to section 153. The coupling 157 permits a purely axial movement of the valve stem means 153 when the valve stem means 131 is rotated. To ensure axial movement of the valve stem portion 153, the valve shutter 137 is provided with guide slots 159 adapted to receive therein the keys 161 which extend radially inwardly from the interior wall 149 of the valve chamber 121. In addition to the sealing means 141 disposed in the third valve housing portion 117, valve 111 is provided with a sealing ring 163 in the second housing portion 119. Thus, the housing portions 119 and 117 by means of the sealing means 163 and 141 respectively, defined therein a chamber 165. The chamber 165 is adapted to receive therein a fluid flow which can be used to modify the temperature of the valve member as will be described in detail below. Additionally, the second port means 129 disposed in the valve housing includes both an inlet port and an outlet port 167 and 169 respectively. The conical tip portion 123 of valve 111 can be provided with an overflow means 171 which conducts the overflowing medium into a collecting chamber not illustrated herein from which it can be drawn off as necessary.

It will be readily appreciated by those skilled in the art that while certain figures have been described specifically in conjunction with one or the other embodiments of this invention, the several unique features of each embodiment can be selectively incorporated within the other embodiment. This can be seen in FIG. 3 in which a somewhat hybrid embodiment of the present invention is illustrated.

Turning now to FIG. 3 there is schematically illustrated in simplified form a sampling valve 211 which incorporates selected features of this invention as described in connection with FIGS. 1 and 2. The sampling valve 211 includes a valve housing 213 which defines a valve chamber 215 therein. A valve stem means 217 has a valve shutter 219 disposed at one end thereof and an actuator means 221 such as a hand wheel disposed at the other end. A bore or channel 223 is generally axially disposed within the stem means to provide communication with the valve chamber 215. The sampling site is typically located in an outlet pipe 225 which directly follows a reactor of a coal gasification plant. The wall of the outlet pipe in which the sampling valve is mounted is indicated at 226. The configuration shown in FIG. 3 provides two pipes 224 and 227 in connection with the second valve chamber which was shown in FIG. 2 at 165. Through the use of two pipes 224 and 227, it is possible, at various positions in the recesses for the seals 163 and 141, to obtain the required pressure reduction or temperature control (see FIG. 2).

The pipe 228 leads via various intermediate valves through a sampling bottle 229 which is advantageously followed by a storage tank 231. For the purpose of clarity the various intermediate valves associated with the pipes of the schematic diagram will not be individually identified. The pipe 228 is provided with branches 233, 235 and 237. The flushing agent or heating medium can be fed via the branch pipes 233 and 235 to a pipe 239 which is connected to the valve stem means conduit 223 of the valve stem means 217 by means of a suitable coupling 241. By this means the flushing agent or heating medium can be passed through the valve chamber 215 and fed into the circuit via the pipe 228 which is in communication with the second port means of the valve housing.

The branch pipe 237 splits in two pipes 243 and 245 with pipe 245 leading directly to the reservoir 249 which has an internal heater, while pipe 243 leads to the reservoir 249 via and intermediate filter 251. In addition, pipe 245 has branches 253 and 255, of which branch 253 leads back to branch 233 and branch 255 arrives via a reservoir 257 with a built in cooler either to the reservoir 249 or, via pipe 227 to serve as a seal protector within the valve housing. (The seal protection would be effected via fluid flow through chamber 165 of the sampling valve 111 shown in FIG. 2).

Reservoir 249 is connected via an intermediate pressure pump 259 to pipe 239 which lead to the valve stem means. As should be readily appreciated, various flow paths can be coordinated through the selected actuation of the various intermediate control valves shown herein.

In the event of a contaminated sampling valve, preheated oil or solvent is conveyed, depending on requirements, via lines 228 and/or 239, into the valve chamber 215 of the sampling valve 211, where it dissolves any solids present. By securing all remaining control valves, the contaminated solution is fed via pipes 228 and branches 237 and 243 to the filter 251. The oil or solvent which is cleaned in the filter 251 is conveyed into the reservior 249 for further disposition.

Should the sampling valve be cold, the oil or solvent present in the reservoir 249 is heated therein and the valve is acted upon via pipes 239 and 228 until the valve has reached the desired temperature. The oil or solvent leaving the sampling pipe via line 228 is conveyed via branch 237, the pipe 245 and the branch 255. Through this process, the oil or solvent passes through the reservoir 257 where it can be cooled according to the requirements of the process. The heating of the sampling valve as described above is particularly important when the crude gas being sampled is at especially high temperatures and/or pressures for which the conventional sealing systems employed in the valve are no longer adequate, so that the return flow, after being suitably cooled and having its pressure suitably reduced, is passed through the pipes 224 and 227 in order to protect the seal system.

For securing a desired sample of the constituent within the pipe 225, the valve which has been cleaned and brought up to the desired temperature by means of an inert heating agent is connected by means of pipe 228 to the sampling bottle 229, and the remaining pipes are closed and connector 241 is uncoupled. With the sampling valve opened, the crude gas then passes through the opening in the upper portion of the valve housing into the valve chamber and eventually into the sampling bottle 229. At the same time, an electric resistance heater, which is housed, if so desired, in the stem means of the sampling valve as at 71 in FIG. 1 and 171 in FIG. 2, ensures that the required temperature of the sampling valve is maintained. The resistance heater can be cojointly used to release unforeseen condensation with flowing flushing agent.

The invention is not to be taken as limited to all the details that are described hereinabove, since modifications and variations thereof may be made without departing from the spirit or scope of the invention.

What is claimed is:

1. An improved sampling valve for use in a fixed bed reactor coal gasification process comprising: a valve housing defining a first valve chamber and a second valve chamber, said first valve chamber with a first opening at one end thereof through which a sample of a constituent of interest enters said first valve chamber and a second opening remote from said first opening through which said sample is removed from said first valve chamber; a valve stem means operatively associated with said valve housing for selectively opening and closing said first valve chamber opening, said valve stem means including a valve shutter means at one end thereof which cooperates with said first opening and a generally axial bore extending from the other end of said valve stem means to said shutter means an in communication with said first valve chamber through said shutter means, said valve housing also defining said second chamber through which said valve stem means passes and third and fourth, second chamber openings through which a medium can be introduced into said second chamber and removed therefrom, said valve housing including seal means operatively disposed therein to isolate said first valve chamber from said second valve chamber, wherein a first medium can be introduced into said first valve chamber when said first opening is closed by means of said valve stem means bore and said first medium can be removed from said first valve chamber through said second opening, and wherein a second medium can be introduced into said second chamber and removed therefrom via said third and fourth second chamber openings.

2. The sampling valve according to claim 1 wherein the valve housing comprises a first portion and a second portion and the first opening of the first valve chamber is in said first portion.

3. The sampling valve according to claim 2 wherein the second valve housing portion defines the second opening and includes a bore therein with which the valve stem means is operatively associated.

4. The sampling valve according to claim 3 wherein the second valve housing second portion bore includes a circumferentially disposed groove therein which defines a seat for a seal means which cooperates with the valve stem means.

5. The sampling valve according to claim 4 wherein the valve housing second portion bore includes a threaded portion and the valve stem means includes a threaded portion which cooperate to effect the axial displacement of the valve shutter means with respect to the first opening.

6. The sampling valve according to claim 1 including resistance heater means disposed in the valve stem means.

7. An improved sampling valve for use in a fixed bed reactor coal gasification process comprising a valve housing defining a first valve chamber with a first opening at one end thereof through which a sample of a constituent enters said first valve chamber and a second opening remote from said first opening through which said sample is removed from said first valve chamber and a valve stem means operatively associated with said valve housing for selectively opening and closing said first valve chamber opening, said valve means including a valve shutter means at one end thereof which cooperates with said first opening, said valve housing also defining a second chamber and including seal means operatively disposed therein to isolate said first valve chamber from said second chamber, said valve stem means passing through said second chamber, and said valve housing also defining third and fourth, second chamber openings through which a medium can be introduced into said second chamber and removed therefrom, and wherein said valve stem means includes a generally axial bore extending from the other end of said valve stem means to said valve shutter means and in communication with said first valve chamber through said valve shutter means, wherein a medium can be introduced into said first valve chamber when the first opening is closed by means of said valve stem means bore, and said medium can be removed from said first valve chamber through said valve chamber second opening.

* * * * *